United States Patent
Isab et al.

(10) Patent No.: US 10,358,456 B2
(45) Date of Patent: Jul. 23, 2019

(54) PLATINUM(II) COMPLEXES WITH SELONE LIGANDS AND METHOD OF USE

(71) Applicants: KING FAHD UNIVERSITY OF PETROLEUM AND MINERALS, Dhahran (SA); KING SAUD UNIVERSITY, Riyadh (SA)

(72) Inventors: Anvarhusein A. Isab, Dhahran (SA); Muhammad Altaf, Dhahran (SA); Ali Alhoshani, Riyadh (SA); Ali Osman Altoum, Dhahran (SA); Mohammed Yagoub Jomaa, Dhahran (SA)

(73) Assignees: King Fahd University of Petroleum and Minerals, Dhahran (SA); King Saud University, Riyadh (SA)

( * ) Notice: Subject to any disclaimer, the term of this patent is extended or adjusted under 35 U.S.C. 154(b) by 0 days.

(21) Appl. No.: 15/933,076

(22) Filed: Mar. 22, 2018

(65) Prior Publication Data

US 2018/0273566 A1 Sep. 27, 2018

Related U.S. Application Data

(60) Provisional application No. 62/474,766, filed on Mar. 22, 2017.

(51) Int. Cl.
| | |
|---|---|
| *C07F 15/00* | (2006.01) |
| *A61K 31/282* | (2006.01) |
| *A61K 31/555* | (2006.01) |
| *A61K 45/06* | (2006.01) |
| *A61P 35/00* | (2006.01) |

(52) U.S. Cl.
CPC ........ *C07F 15/0093* (2013.01); *A61K 31/282* (2013.01); *A61K 31/555* (2013.01); *A61K 45/06* (2013.01); *A61P 35/00* (2018.01)

(58) Field of Classification Search
CPC . C07F 15/0093; A61K 31/282; A61K 31/555; A61P 35/00
USPC .................. 548/316.4; 544/315; 540/485
See application file for complete search history.

(56) References Cited

FOREIGN PATENT DOCUMENTS

| JP | 59-190999 | 10/1984 |
|---|---|---|
| JP | 2-28190 | 1/1990 |

OTHER PUBLICATIONS

Wazeer et al. Magn. Reson. Chem. 2003; 41: 1026-1029.*
Cecil Textbook of Medicine, edited by Bennet, J.C., and Plum F., 20th edition,vol. 1, 1004-1010 1996.*
Freshney et al.,Culture of Animal Cells, A Manual of Basic Technique, Alan R. Liss, Inc., 1983, New York, p. 4.*
Dermeret al., Bio/Technology, 1994, 12:320.*
Golub et al., Science, 286, 531-537, 1999.*
Altoum et al. Journal of Coordination Chemistry (2017), 70(6), 1020-1031; CA 166: 291994, 2017. CAPLUS Abstract provided.*
Ahmad, S., et al., "Synthesis, Crystal Structure and Anticancer Activity of Tetrakis(N-Isopropylimidazolidine-2 Selenone)Platinum(II) Chloride", Journal of Molecular Structure, vol. 1152, 3 Pages total, (Jan. 15, 2018) (Abstract only).
Altoum, A.O.S., et al., "Synthesis, Structural Characterization and Cytotoxicity Evaluation of Platinum(II) Complexes of Heterocyclic Selenones", Polyhedron, vol. 128, 3 Pages total, (May 28, 2017) (Abstract only).
Altoum, A.O.S., et al., "Synthesis, Characterization, and In Vitro Cytotoxicity of Platinum(II) Complexes of Selenones [Pt(Selenone)2CL2]", Journal of Coordination Chemistry, vol. 70, Issue 6, 7 Pages total, (Feb. 6, 2017) (Abstract only).
Chauhan, R.S., et al., "Oxidative Addition Reactions of Nicotinamide Based Organoselenium Compounds on [M(PPh )] (M=Pd or Pt): An Insight Study for the Formation of Several Isolable Products", Journal of Organometallic Chemistry, vol. 723, 4 Pages total, (Jan. 1, 2013) (Abstract only).
Feeder, N., et al., "Chalcogen Abstraction from Dithiadiazolyl and Deselenadiozolyl Platinum Complexes: Crystal Structure of a Novel Metalla-Heterocycle", Journal of the Chemical Society, Dalton Transactions, Issue 24, 5 Pages total, (1998) (Abstract only).

* cited by examiner

*Primary Examiner* — Venkataraman Balasubramanian
(74) *Attorney, Agent, or Firm* — Oblon, McClelland, Maier & Neustadt, L.L.P.

(57) ABSTRACT

Platinum(II) complexes with various selones (L) having the general formula $PtL_2Cl_2$ are disclosed. The platinum(II) complexes of the invention inhibit growth of cancer cells in vitro and are useful for treatment of proliferative disorders such as cancers and/or tumors.

10 Claims, 2 Drawing Sheets

PLATINUM(II) COMPLEXES WITH SELONE LIGANDS AND METHOD OF USE

This application claims priority from Provisional Application 62/474,766, filed Mar. 22, 2017.

STATEMENT OF FUNDING ACKNOWLEDGEMENT

This project was funded by King Fahd University of Petroleum and Minerals (KFUPM), DSR, under the project number IN141029.

STATEMENT REGARDING PRIOR DISCLOSURE BY THE INVENTORS

Aspects of this technology are described by the inventor in an article "Synthesis, characterization and in vitro cytotoxicity of platinum(II) complexes of selenones [Pt(selenone)$_2$Cl$_2$]", Journal of Coordination Chemistry, 70, (6) 1020-1031, published online 6 Feb. 2017, which is incorporated herein by reference in its entirety.

BACKGROUND OF THE INVENTION

Technical Field

The present disclosure relates to platinum(II) complexes with antiproliferative or antitumor activities. More specifically, these platinum(II) complexes are platinum(II)-chlorides having selones as co-ligands.

Description of the Related Art

The "background" description provided herein is for the purpose of generally presenting the context of the disclosure. All references cited herein are incorporated by reference. Work of the presently named inventors, to the extent it is described in this background section, as well as aspects of the description which may not otherwise qualify as prior art at the time of filing, are neither expressly or impliedly admitted as prior art against the present disclosure.

Since the approval of cisplatin for clinical use to treat cancer in 1978, platinum compounds continue to be among the most efficient anticancer drugs available [Johnstone et al. Chem. Rev., 2016, 116, 3436-3486; Shahana Dilruba and, Ganna V. Kalayda, Cancer Chemotherapy and Pharmacology, 2016, 77 (6), pg. 1103-1124; Wheate et al, 2010; 39: 8113-8127; Medici et al. Chem. Rev. 284 (2015) 329-350; Wang et al. Chem. Soc. Rev., (2013) 42: 202-224; Jung et al. Chem. Rev. 107 (2007) 1387-1407; Wong et al. Nature Rev. Drug Disc. 4 (2005) 307-320; Kelland, L. (2007) Nature Reviews Cancer, 7: 573-584; Jan Reedijk, Eur. J. Inorg. Chem. 2009, 1303-1312; and Dasari et al. Eur. J. Pharmacol. 2014, 364-378.]. Despite the wide spectrum of anticancer activity shown by the platinum compounds their therapeutic efficacy is somewhat compromised by the occurrence of serious side effects [Dasari et al. Eur. J. Pharmacol. 2014, 364-378; Florea et al. Cancers 2011, 3, 1351-1371 (toxicity); Hartmann et al. (2003) 4, 889-901; and Piccolini et al. Cell Biol Toxicol (2013) 29:339-353] and development of resistance [Galluzzi et al. Oncogene (2012) 31, 1869-1883; D. J. Stewart, Crit. Rev. Oncol. Hematol. 63 (2007) 12-31; and Zisowsky et al. Biochem. Pharmacol. 2007, 73, 298]. The ability of platinum complexes to significantly inhibit tumor growth is a direct result of their reaction with nuclear DNA [Chaney et al. Crit. Rev. Oncol. Hematol. 53 (2005) 3-11; Zutphen et al. Coord. Chem. Rev. 249 (2005) 2845-2853; Jamieson et al. (1999). Chemical Reviews, 99: 2467-2498; Ahmad et al. Transition Metal Chemistry (2006) 31, 1003-1016; S. Ahmad, Chemistry & Biodiversity 7 (2010) 543-566; Fuertes et al. Curr. Med. Chem. (2003) 10, 257; and Komeda, S. (2011) Metallomics, 3: 650-655.]. However, prior to binding to DNA, aquation of the drug is required [Ahmad et al. (2006) and Ahmad et al. (2010)]. Aquation is usually the rate-determining step in the reaction of platinum (II) complexes with DNA [Knox et al. Cancer Res., 46, 1972 (1986]. Due to the low concentration of chloride, cisplatin undergoes aquation inside the cell and is converted to the highly reactive species $[Pt(NH_3)_2Cl(H_2O)]^+$, which forms mainly 1,2-GpG intrastrand adducts with DNA. Adduct formation leads to inhibition of transcription and replication of DNA, and ultimately to tumor cell apoptosis. Carboplatin displays a mode of action similar to that of cisplatin, but it is less reactive than cisplatin [Mlcouskova et al. J Biol Inorg Chem (2012) 17:891-898]. The rate of aquation of the leaving group of carboplatin, namely the 1,1 cyclobutanedicarboxylate ligand, is nearly half of cisplatin. Consequently, carboplatin is used at higher dosage and has fewer side effects compared to cisplatin during clinical treatment [Boulikas et al. Oncol. Rep. 10 (2003) 1663]. The strong and irreversible binding of cisplatin to intracellular thiolate ligands is believed to deactivate the drug by preventing it from reaching the biological target, DNA. Sulfur containing biomolecules such as cysteine, methionine, and glutathione have high affinity for platinum(II) complexes and ligate rapidly to $Pt^{+2}$ ions that enter the cell [Ahmad (2006); J. Reedijk, Chem. Rev. 1999, 99, 2499; and J. Reedijk, Chem. Commun. 1996, 801]. This preferential binding of platinum to sulfur donors rather than the bases of DNA causes resistance to cisplatin [Galluzzi et al. (2012), Stewart (2007), Liu et al. J. Inorg. Biochem. 2004, 98, 702; and Messori et al. Coord. Chem. Rev., 315 (2016) 67-89].

In view of the forgoing, one object of the present disclosure is to provide a new class of platinum(II) complexes having cytotoxic properties against cancer and/or tumors with reduced side effects.

BRIEF SUMMARY OF THE INVENTION

According to a first aspect of the invention, the current disclosure relates to a platinum (II) complex having formula PtL$_2$Cl$_2$ of, wherein L has formula (I)

(I)

or a salt thereof, a solvate thereof, a tautomer thereof, a stereoisomer thereof, or a mixture thereof; wherein $R_1$ and $R_2$ are independently selected from the group consisting of a hydrogen, $NR_3R_4$, $OR_3$, $SR_3$, $SeR_3$, an optionally substituted alkyl, an optionally substituted alkylene, an optionally substituted cycloalkyl, an optionally substituted aryl, and an optionally substituted arylalkyl; and $R_3$ and $R_4$ are independently hydrogen, an optionally substituted alkyl, an optionally substituted cycloalkyl, an optionally substituted heterocyclic, an optionally substituted aryl, and an optionally substituted arylalkyl; or $R_1$ and $R_2$ are linked together forming an optionally substituted ring selected from the group consisting of a four membered ring, a five membered ring, a six membered ring, a seven membered ring, or an eight membered ring.

In a preferred embodiment, $R_1$ and $R_2$ are linked together forming an optionally substituted ring.

Another preferred embodiment, the ring is selected from the group consisting of a four membered ring, a five membered ring, a six membered ring, a seven membered ring, or an eight membered ring.

Another preferred embodiment the ring is saturated or unsaturated cycloalkyl ring or saturated or unsaturated heterocylic ring.

A more preferred embodiment, formula (I) is selected from the group consisting of:

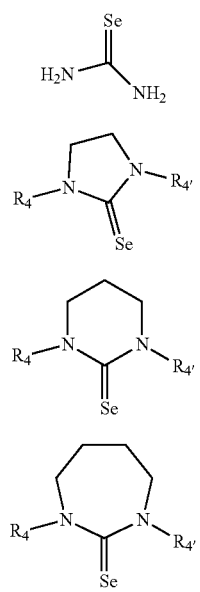

wherein $R_4$ and $R_{4'}$ are independently hydrogen, methyl, ethyl, propyl, isopropyl, butyl, isobutyl, t-butyl, pentyl, isopentyl, phenyl, benzyl.

A second aspect of the invention is directed to a synthetic method for making $PtL_2Cl_2$ complex of the invention, said method comprising:
(a) adding a solution of tetrahaloplatinate(II) dissolved in aprotic solvent to a solution of a compound of formula I in a solvent under inert gas to form a reaction mixture, and
(b) stirring the reaction mixture to form a precipitate.

A preferred embodiment of the method comprises filtering the precipitated $PtL_2Cl_2$ complex.

Another preferred embodiment of the method comprising stirring the reaction mixture in a dry box for a time ranging between 5 min to 5.0 hours, more preferably, 0.5 to 3.0 hours, and even more preferably, 1.0-2.0 hours, and most preferably one hour.

A third aspect of the invention is related to a pharmaceutical composition comprising the platinum(II) complex of the invention and a pharmaceutically acceptable carrier and/or excipient.

A preferred embodiment, the pharmaceutical composition comprises 0.1-400 μM of the platinum(II) complex relative to the total volume of the composition.

Another preferred embodiment, the pharmaceutical composition comprises one or more carrier and/or excipient selected from the group consisting of a buffer, an inorganic salt, a fatty acid, a vegetable oil, a synthetic fatty ester, a surfactant, a sugar, a polymer, and combination thereof.

Another preferred embodiment, the pharmaceutical composition further comprises a chemotherapeutic agent.

A more preferred embodiment, the pharmaceutical composition comprising a the platinum(II) complex of the invention wherein L is selected from the group consisting of formula (Ia)-(Id)

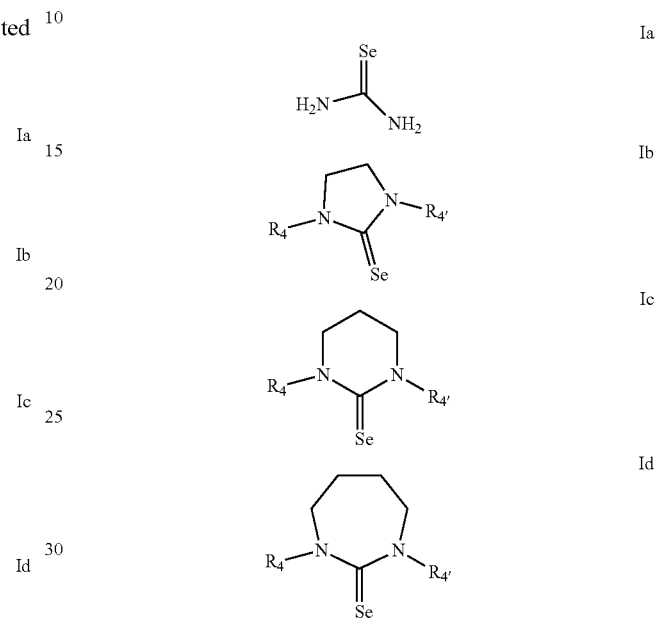

wherein $R_4$ and $R_{4'}$ are independently hydrogen, methyl, ethyl, propyl, isopropyl, butyl, isobutyl, t-butyl, pentyl, isopentyl, phenyl, benzyl; and and a pharmaceutically acceptable carrier and/or excipient.

The most preferred embodiment, the pharmaceutical composition further comprises a chemotherapeutic agent.

A fourth aspect of the invention is related to a method for treating a proliferative disorder, comprising administering to a subject in need of therapy sufficient amount of a pharmaceutical composition comprising the platinum (II) complex of the invention, wherein the proliferative disorder is cancer and/or tumor.

A preferred embodiment of the method of treatment, 1-300 mg/kg of the platinum complex of is administered per body weight of the subject.

Another preferred embodiment of the method treating a proliferative disorder comprises administering to a subject in need of therapy a sufficient amount of the pharmaceutical composition comprising a platinum complex $PtL_2Cl_2$, wherein L is selected from the group consisting of formula (Ia)-(Id)

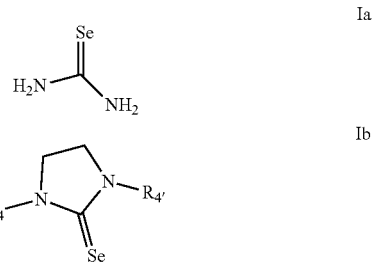

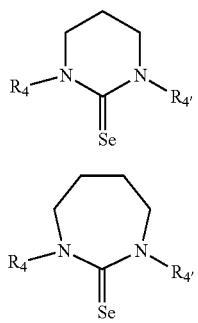

wherein R$_4$ and R$_{4'}$ are independently hydrogen, methyl, ethyl, propyl, isopropyl, butyl, isobutyl, t-butyl, pentyl, isopentyl, phenyl, benzyl; and a pharmaceutically acceptable carrier and/or excipient.

A more preferred embodiment of the method, the cancer is at least one selected from the group consisting of ovarian cancer, cervical cancer, testicular cancer, colon cancer, bladder cancer, breast cancer, non-small cell lung cancer, esophageal cancer, endometrial cancer, head and neck cancer, osteogenic sarcoma.

The most preferred embodiment of the method of treatment, the cancer is cervical cancer, breast cancer, or colon cancer.

Another preferred embodiment of the method of treatment, the proliferative disorder is a tumor.

A more preferred embodiment, the tumor is central nervous system tumor or germ cell tumor.

The most preferred embodiment of the method, the subject of treatment is a mammal, in particular, human.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
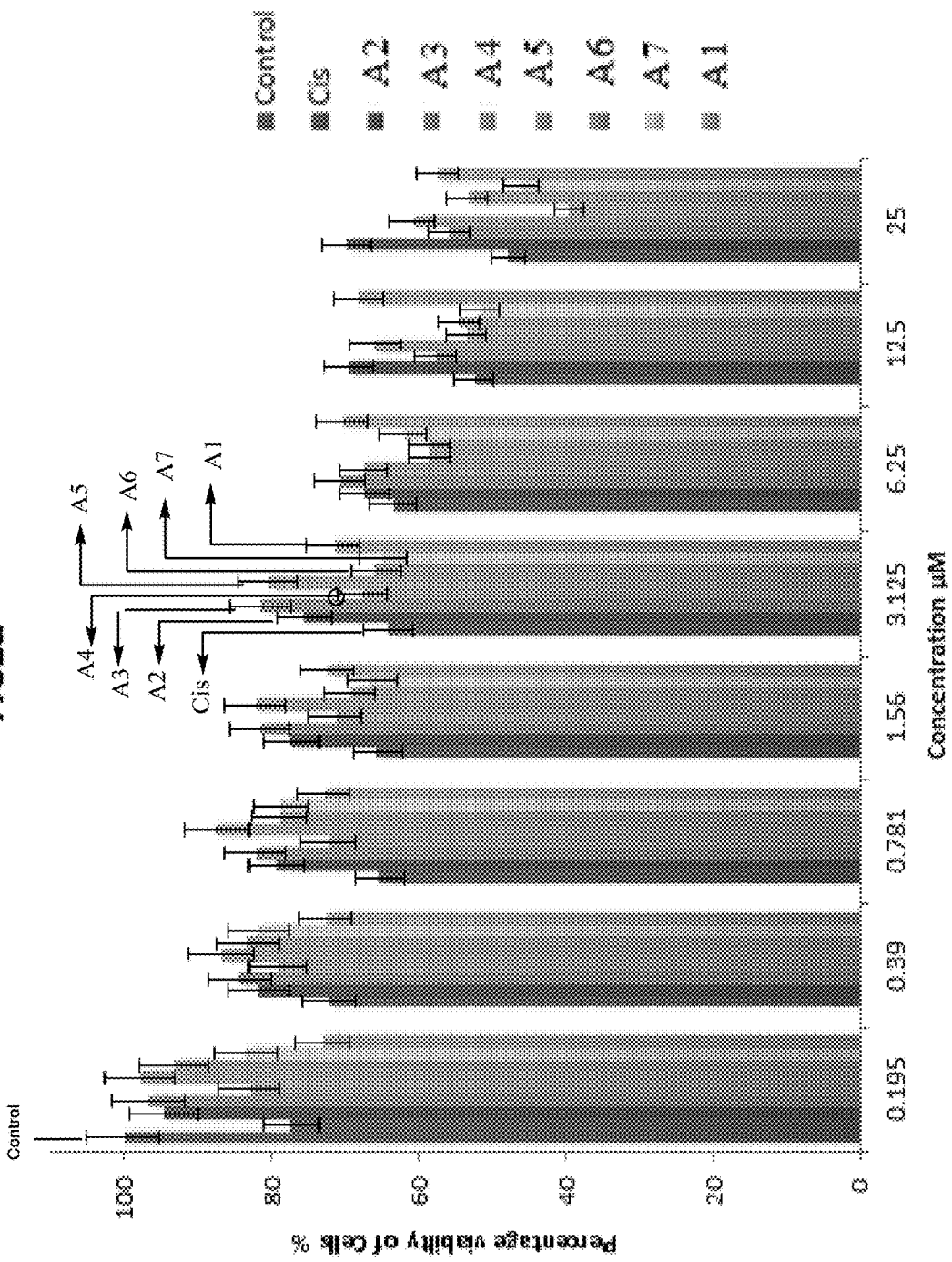
FIG. 1: Effect of concentration of PtL$_2$Cl$_2$ complexes, wherein L is selected from compounds 1-7, and cisplatin (Cis) in μM on the percentage viability of HeLa. The complexes are designated A1-A7 in the Figure.

Embodiments of the present disclosure will now be described more fully hereinafter with reference to the accompanying drawings, in which some, but not all embodiments of the disclosure are shown.

As used herein, the terms "compound" and "complex" are used interchangeably, and are intended to refer to a chemical entity, whether in a solid, liquid or gaseous phase, and whether in a crude mixture or purified and isolated.

Unless otherwise specified, "a" or "an" means "one or more".

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethyl formamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol (PEG), polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those skilled in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), enamine and enamine and anomers of reducing sugars.

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds.

Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, metal complexes such as platinum, and the like can all be present in the compounds, and all such stable isomers are contemplated in the present disclosure. Cis- and trans- (or E- and Z-) stereoisomers of the compounds of the present disclosure wherein rotation around the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. Also, platinum (II) complexes are known to be square or distorted square planer with the platinum (II) ion at the center. Thus, $PtL_2Cl_2$ of the instant invention may be either cis- or trans-complex. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

In this disclosure, the term inert gas refers to any gas that does not react with any component of a reaction mixture of interest. Several inert gases are well-known in the art including nitrogen and nobel gases such as helium and argon.

The present disclosure is further intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}C$ and $^{14}C$, isotopes of nitrogen include $^{14}N$ and $^{15}N$, isotopes of selenium include $^{74}Se$, $^{76}Se$, $^{77}Se$, $^{78}Se$, and $^{80}Se$, and isotopes of oxygen include $^{16}O$, $^{17}O$, and $^{18}O$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

According to a first aspect of the invention, the current disclosure relates to a platinum (II) complex having formula $PtL_2Cl_2$, wherein L has formula (I)

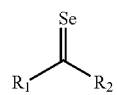

(I)

or a salt thereof, a solvate thereof, a tautomer thereof, a stereoisomer thereof, or a mixture thereof; wherein $R_1$ and $R_2$ are independently selected from the group consisting of hydrogen, $NR_3R_4$, $OR_3$, $SR_3$, $SeR_3$, an optionally substituted alkyl, an optionally substituted alkylene, an optionally substituted cycloalkyl, an optionally substituted aryl, and an optionally substituted arylalkyl; and $R_3$ and $R_4$ are independently hydrogen, an optionally substituted alkyl, an optionally substituted cycloalkyl, an optionally substituted heterocyclic, an optionally substituted aryl, and an optionally substituted arylalkyl; or $R_1$ and $R_2$ are linked together forming an optionally substituted ring selected from the group consisting of a four membered ring, a five membered ring, a six membered ring, a seven membered ring, or an eight membered ring.

As used herein, a selone or a selenone is the structural analog of any organic molecule containing a carbonyl group in which the carbonyl oxygen atom is replaced with selenium atom. Without any limitation, examples of selone are seleno urea $[SeC(NH_2)_2]$ and derivatives thereof, seleno ketones, seleno aldehydes, selone esters and thio esters, seleno-amides, seleno-peptides, and mono- and diseleno carboxylic acid. Selones are well-known in the art as natural products as well as synthetic products. Both 5-methylaminomethyl-2-selenoueidine and selenoneine, the seleno analog or ergothionine are isolated from organisms [Reich et al. ACS Chem. Biol. (2016) 11, 821-841, which is incorporated herein in its entirety by reference]. Many selenoamides and selenopeptides have been described along with method of their synthesis and characterization [see for example: Toshiaki et al. J. Org. Chem (2015) 80 (13), 6903-6907; Hussain et al. Archives for Organic Chemistry, Volum 2008, Issue 13, pages 129-136; and Vishwanatha et al. J. Org. Chem. (2012) 77 (6), 2689-2702; which are incorporated herein by reference in their entirety]. Taher et al. [Organometallicus (2011) 30 (21), 5943, which is incorporated herein in its entirety by reference] reported the synthesis of mono- and diseleno analogs of carboxylic acids. Anouri et al. [Angew. Chem. Intr. Ed 49, 7530-7533, which is incorporated herein in its entirety by reference] discloses the preparation of the diselenobenzoquinone and indicated the compound is stable. Lyubovskaya et al. [Bull. Acad. Sci. USSR, Div. Chem. Sci (1976) 25 (1), 168-170, incorporated herein by reference in its entirety] disclose the synthesis of 1,3-diseleno-2-selenone, compound A shown below. Also, heterocyclic compound containing the double bonded carbon to selenium are reported in U.S. Pat. No. 6,448,409 which is incorporated herein by reference in its entirety, see in particular the selenium-based cyclocarbamate compound B shown below.

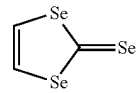

Compound A

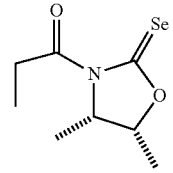

Compound B

Schmidt and Silks [Product Class 11: "Seleno and Telluro Carbonic Acid Derivatives" Chapter 11, In Science of Synthesis: Houben Weyl Method of Molecular Transformation, J. G. Knight, Volum 18, George Thiem Verlag Publisher (2014); incorporated herein by reference in its entirety] describe general methodology in the preparation of the selone derivatives of carbonic acid. Seleno urea is often used as a precursor in the synthesis of selenium-containing heterocycles, which may exhibit potential anti-inflammatory and/or antitumor activities. As a result of its electron-donating amino groups, selenourea can also act as an effective ligand for complexation with transition metals.

In a preferred embodiment, $R_1$ and $R_2$ are linked together forming an optionally substituted ring system. The ring system may be a saturated or unsaturated optionally substituted cycloalkyl or heterocyclic of any size. The ring system may be a four membered ring, a five membered ring, a six membered ring, a seven membered ring, or an eight membered ring. The saturated or unsaturated cycloalkyl ring may be a four membered ring, a five membered ring, a six membered ring, a seven membered ring, an eight membered ring or larger. Examples of the cycloalkyl ring systems are cyclobutyl, cyclopentyl, cyclohexyl, cycloheptyl, cyclooctyl, or even larger ring system with or without one or more double or triple bonds. Similarly, the heterocyclic ring system may be saturated or unsaturated of any size having one or more hetero atoms. The heteroatoms may be the same such as nitrogen, oxygen, tellurium, selenium, and sulfur, or different including any combination of heteroatoms such as oxygen, sulfur, tellurium, selenium, or nitrogen. A more preferred embodiment of the invention, formula (I) is selected from the group consisting of:

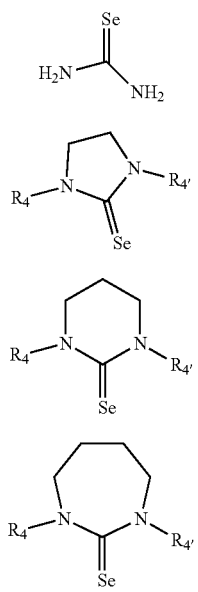

wherein $R_4$ and $R_{4'}$ are independently selected from the group consisting of a hydrogen, an optionally substituted alkyl, an optionally substituted cycloalkyl, an optionally substituted aryl, and an optionally substituted arylalkyl. In a more preferred embodiment, $R_4$ and $R_{4'}$ are independently hydrogen, methyl, ethyl, propyl, isopropyl, butyl, isobutyl, t-butyl, pentyl, isopentyl, phenyl, benzyl.

As used herein, the term "substituted" refers to at least one hydrogen atom that is replaced with a non-hydrogen group, provided that normal valences are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, aubstituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like.

As used herein, the term "alkyl" unless otherwise specified refers to both branched and straight chain saturated aliphatic primary, secondary, and/or tertiary hydrocarbons of typically $C_1$ to $C_{10}$, preferably $C_1$ to $C_6$, more preferably $C_2$ to $C_3$, and specifically includes, but is not limited to, methyl, trifluoromethyl, ethyl, n-propyl, isopropyl, n-butyl, sec-butyl, isobutyl, t-butyl, pentyl, isopentyl, neopentyl, hexyl, isohexyl, 3-methylpentyl, 2,2-dimethylbutyl, and 2,3-dimethylbutyl.

As used herein, the term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "alkenyl" refers to a straight, branched, or cyclic hydrocarbon fragment containing at least one C=C double bond. Exemplary alkenyl groups include, without limitation, 1-propenyl, 2-propenyl (or "allyl"), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, and 9-decenyl.

The term "alkynyl" refers to a straight or branched hydrocarbon fragment containing at least one C≡C triple bond. Exemplary alkynyl groups include, without limitation, ethynyl, 1-propynyl, 2-propynyl (i.e., propargyl), 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonynyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, and 9-decynyl.

The term "alkoxy" refers to a straight or branched chain alkoxy including, but not limited to, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy.

As used herein, the term "aryl" unless otherwise specified refers to functional groups or substituents derived from an aromatic ring including, but not limited to, phenyl, biphenyl, napthyl, anthracenyl, thienyl, and indolyl.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "alkanoyl", as used herein, refers to an alkyl group of specified number of carbon atoms that is bound to an oxygen atom through a double bond. Exemplary alkanoyl groups include, but are not limited to, formyl, acetyl, propanoyl, butyryl, and hexanoyl.

The term "aroyl" as used in this disclosure refers to an aromatic carboxylic acyl group includes, for example, benzoyl, 1-naphthoyl, and 2-naphthoyl.

The term "halogen", as used herein, means fluorine, chlorine, bromine, and iodine.

According to a second aspect, the present invention is directed to a synthetic method for making $PtL_2Cl_2$ complex of the invention, said method comprising:
(a) adding a solution of tetrahaloplatinate(II) in a polar aprotic solvent to a solution of a compound of formula I in a solvent under inert gas to form a reaction mixture, and
(b) stirring the reaction mixture to form a precipitate.

Tetrahaloplatinate(II) may be dissolved in any solvent that is capable to dissolve it under its boiling point. The solvent may be any polar protic or aprotic solvent. The protic solvents includes but not limited to alcohols such as methanol, ethanol, and propanol. In another embodiment, the solvent is a polar aprotic solvent such as acetonitrile, dimethylformamide (DMF), tetrahydrofurane (THF), dioxane and dimethyl sulfoxide (DMSO). Similarly, the selone compound of formula I can be dissolved in any solvent in which formula I is soluble, preferably a polar solvent such as acetonitrile, DMD, DMSO, THF, or alcohols including methanol, ethanol, propanol, isopropanol, butanol, pentanol, hexanol, or any isomer thereof. The most preferred solvent is methanol. In a preferred embodiment of the method, tetrahaloplatinate(II), preferably tetrachloroplatinate(II) is dissolved in hot acetonitrile and the selone compound of formula I is dissolved in methanol. The method may require agitating or stirring the reaction mixture by any method well-known in the art. Methods of agitating or steering a reaction mixture include, without limitation, using an agitator, a vortexer, a rotary shaker, a magnetic stirrer, a centrifugal mixer, or an overhead stirrer. In one embodiment, the mixture is mixed with a spatula. In another embodiment, the mixture is agitated by sonication in an ultrasonic bath or with an ultrasonic probe. In another embodiment, the mixture is left to stand without being stirred. In a preferred embodiment, the mixture is agitated using a magnetic stirrer with a rotational speed of at least 250 rpm, preferably at least 400 rpm, more preferably at least 600 rpm. The steering or agitating of reaction mixture is preferably carried out in dry box for a time ranging between 5 min to 5.0 hours, more preferably, 0.5 to 3.0 hours, and even more preferably, 1.0-2.0 hours, and most preferably one hour.

In a preferred embodiment, the method may be carried out at ambient temperature or at elevated temperature as long as the reaction mixture is kept in oxygen and water free environment. Typically, potassium tetracholoridoplatinate (II) and selone compound are mixed in 1:2 molar ratio, respectively, and the mixture is stirred to precipitate the complex. The reaction can be carried out on any scale ranging from laboratory scale in the range 0.1-1.0 mol to industrial scale of 10-20 mol of potassium tetracholoridoplatinate(II) or even larger quantities. The yield of the complex is at least 40%, preferably at least 50%, preferably at least 55%, preferably at least 60%, preferably at least 70%, preferably at least 80% by weight, and most preferably at least 90% based on the potassium tetracholoroplatinate(II).

The product $PtL_2Cl_2$ complex of the method may be soluble in the reaction mixture and may be isolated and purified by well-known methods in the art including, but not limited to chromatography and crystallization. In a preferred embodiment of the method, the product $PtL_2Cl_2$ complex of the method is precipitated in the reaction mixture and isolated by filtration or centrifugation. The product may be further decolorized, recrystallized and dried.

A third aspect of the invention is directed to compositions, in particular, a pharmaceutical composition, wherein the active ingredient is one or more $PtL_2Cl_2$ complexes of the invention.

As used herein, a "composition" or a "pharmaceutical composition" refers to a mixture of the active ingredient with other chemical components, such as pharmaceutically acceptable carriers and excipients. One purpose of a composition is to facilitate administration of the $PtL_2Cl_2$ complex of the invention to a subject. Pharmaceutical compositions of the present disclosure may be manufactured by processes well-known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, the $PtL_2Cl_2$ complex wherein L represented by Formula (I), a salt thereof, a solvate thereof, a tautomer thereof, a stereoisomer thereof, or any mixtures thereof.

In one or more embodiments, the pharmaceutical composition comprises at least 0.01 wt %, 0.05 wt %, 0.1 wt %, 0.5 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 99 wt %, or 99.9 wt % of the $PtL_2Cl_2$ complex relative to the total weight of the composition. The pharmaceutical composition may contain 0.1-400 µM, 1-300 µM, preferably 10-200 µM of $PtL_2Cl_2$ complex of the invention relative to the total volume of the composition. In some embodiments, the composition comprises up to 0.1 wt %, 1 wt %, 5 wt %, or 10 wt % of a pharmaceutically acceptable salt of the $PtL_2Cl_2$ complex. In some embodiments, the composition comprises up to 0.1 wt %, 1 wt %, 5 wt %, or 10 wt % of a pharmaceutically acceptable solvate of the $PtL_2Cl_2$ complex. Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO).

In some embodiments, the ability of the active ingredient to reduce the viability of cancer cells may be determined by contacting the pharmaceutical composition with the cancer cells and then performing cell viability assays. Methods of such assays include, without limitation, ATP test, Calcein AM assay, clonogenic assay, ethidium homodimer assay, Evans blue assay, fluorescein diacetate hydrolysis/Propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, and TUNEL assay. In a preferred embodiment, a MTT assay is used.

In some embodiments, the cancer cells are derived from human cancer cell lines, including, but not limited to, colon cancer cell lines, e.g., HCT15, MDST8, GP5d, HCT116, DLD1, HT29, SW620, SW403 and T84, lung cancer cell lines, e.g., A549, SHP-77, COR-L23/R, and NCI-H69/LX20, breast cancer cell lines, e.g., MDA-MB-231, MCF7, T47D, and VP303, cervical cancer cell Lines, e.g., HeLa DH, HtTA-1, HRS, and C-4I, ovarian cancer cell lines, e.g., A2780, A2780cis, OV7, and PEO23, and skin cancer cell lines, e.g., C32TG, A375, and MCC26. In other embodiments, the cancer cells are collected from a human patient who is at risk of having, is suspected of having, has been diagnosed with, or is being monitored for recurrence of at least one type of cancer, preferably colon cancer, lung cancer, cervical cancer, testicular cancer, and/or breast cancer. In at least one embodiment, cisplatin-resistant cancer cells are used. These cells may be generated by culturing cancer cells with low doses of cisplatin in order to build their resistance to cisplatin while maintaining cell viability. Examples of cisplatin-resistant cancer cells include, but are not limited to, A549 cisplatin-resistant lung cancer cells, MCF-7 cisplatin-resistant breast cancer cells, A2780cis cisplatin-resistant ovarian cancer cells, and SGC7901cis cisplatin-resistant gastrointestinal cancer cells.

As used herein, the terms "sufficient amount" or "cytotoxic effective amount" are used interchangeably, and are intended to refer to to a concentration of the active ingredient that reduces the viability of the cancer cells by at least 5%, 10%, 15%, 20%, 30%, 40%, 50%, 60%, 70%, 80% or 90%, relative to cancer cells not treated with the active ingredient. The reduction in viability may occur no more than 10 days, 7 days, 5 days, 3 days, or 2 days after the active ingredient is contacted with the cancer cells. In one embodiment, the cytotoxic effective amount may be the $IC_{50}$ which is a concentration of the active ingredient which causes the death of 50% of cancer cells in 72 hours (3 days). In one embodiment, the $IC_{50}$ of the $PtL_2Cl_2$ complex, the salt thereof, the solvate thereof, the tautomer thereof, the stereoisomer thereof, or the mixture thereof against colon cancer cells is in a range of 0.01-150 μM, preferably 1-70 μM, more preferably 30-40 μM. In another embodiment, the $IC_{50}$ of the $PtL_2Cl_2$ complex, the salt thereof, the solvate thereof, the tautomer thereof, the stereoisomer thereof, or the mixture thereof against lung cancer cells is in a range of 0.01-200 μM, preferably 1-80 μM, more preferably 40-50 μM. In another embodiment, the $IC_{50}$ of the $PtL_2Cl_2$ complex, the salt thereof, the solvate thereof, the tautomer thereof, the stereoisomer thereof, or the mixture thereof against breast cancer cells is in a range of 0.01-120 μM, preferably 1-60 μM, more preferably 40-50 μM.

In some embodiments, other active ingredients in addition to the $PtL_2Cl_2$ complex of the current disclosure may be incorporated into a pharmaceutical composition. In one embodiment, the pharmaceutical composition includes a second active ingredient, such as a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

As used herein, other non-cancerous proliferative disorders that may also be treated by the currently disclosed pharmaceutical composition include, without limitation, atherosclerosis, rheumatoid arthritis, psoriasis, idiopathic pulmonary fibrosis, scleroderma, cirrhosis of the liver, lymphoproliferative disorder, other disorders characterized by epidermal cell proliferation such as verruca (warts), and dermatitis, and benign proliferative breast disease such as ductal hyperplasia, lobular hyperplasia, and papillomas.

The anticancer agent is at least one of a mitotic inhibitor; an alkylating agent; an antimetabolite; a cell cycle inhibitor; an enzyme; a topoisomerase inhibitor; a biological response modifier; an anti-hormone; an antiangiogenic agent such as MMP-2, MMP-9 and COX-2 inhibitor; an anti-androgen; a platinum coordination complex such as oxaliplatin, carboplatin; a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary anticancer agents include, but are not limited to, alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; anti-microtubule agents including etoposide, vinblastine, vincristine, teniposide, docetaxel, paclitaxel, vinorelbine, vindesine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound.

Examples, without limitation, of excipients include calcium carbonate, calcium phosphate, various sugars and types of starch, cellulose derivatives, gelatin, vegetable oils, and polyethylene glycols.

In some embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to an monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectable. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the composition having the $PtL_2Cl_2$ complex disclosed herein, the salt thereof, the solvate thereof, the tautomer thereof, the stereoisomer thereof, or the mixture thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the composition is not a controlled-release composition.

According to a fourth aspect, the current disclosure relates to a method for treating a proliferative disorder, comprising administering the pharmaceutical composition of the second aspect to a subject in need of therapy.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumour size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but is not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

In one or more embodiments, the proliferative disorder is cancer. In some embodiments, the disclosed method of the fourth aspect is for treating cancer of the blood, brain, bladder, lung, cervix, ovary, colon, rectum, pancreas, skin, prostate gland, stomach, breast, spleen, liver, kidney, head, neck, testicle, bone, bone marrow, thyroid gland, or central nervous system. In a preferred embodiment, the cancer is at least one selected from the group consisting of colon cancer, cervical cancer, breast cancer, and lung cancer. In a more preferred embodiment, the cancer is cervical cancer or breast cancer. In the most preferred embodiment, the cancer is cervical cancer or breast cancer.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. White women or a person with (i) certain inherited genes (e.g. mutated BRCA1, BRCA2, ATM, TP53, CHEK2, PTEN, CDH1, STK11, and PALB2), (ii) radiation occurred to one's chest, and/or (iii) exposure to diethylstilbestrol (DES) are at a higher risk of contracting breast cancer. People who (i) smoke or regularly breathe in second-hand smoke, (ii) exposed to carcinogens including, but not limited to polycyclic aromatic hydrocarbons (e. g. benzo[a]pyrene, benz[a]anthracene, and methylated derivatives thereof), asbestos, radioactive substances (e.g., uranium, radon), and/or (iii) inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the compounds and methods described herein. In preferred embodiments, the active ingredient and/or the composition described herein are administered orally.

In one or more embodiments, the pharmaceutical composition administered comprises the $PtL_2Cl_2$ complex where in L is Formula (I), or a salt thereof, a solvate thereof, a tautomer thereof, a stereoisomer thereof, or a mixture thereof, in which $R_1$ and $R_2$ as defined herein.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", "pharmaceutically effective amount" or sufficient amount refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In some embodiments, an effective amount of the platinum(II) complex having the formula $PtL_2Cl_2$, wherein L is Formula (I) is in a range of 1-300 mg/kg, preferably 10-200 mg/kg, more preferably 50-100 mg/kg is administered per body weight of the subject.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be before or after the composition is administered.

A treatment method may comprise administering a pharmaceutical composition containing the $PtL_2Cl_2$ complex of the current disclosure as a single dose or multiple individual divided doses. In some embodiments, the composition is administered at various dosages (e.g. a first dose with an effective amount of 200 mg/kg and a second dose with an effective amount of 50 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, 1 month, 2 months, 3 months, 6 months, 1 year, 2 years, or 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, the size of a tumor after treatment does not reduce but is maintained the same as the tumor size before treatment. Methods of assessing tumor size include, but are not limited to, CT scan, MM, DCE-MRI and PET scan.

In most embodiments, the method further comprises measuring a concentration of a biomarker and/or detecting a mutation in a biomarker before and/or after the pharmaceutical composition comprising the $PtL_2Cl_2$ complex of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary biomarkers for colon cancer include, without limitation, carcinoembryonic antigen (CEA), carbohydrate antigen 242 (CA 242), CA 195, CA 19-9, MSI, and 18qLOH. Exemplary biomarkers for breast cancer include, without limitation, BRCA1, BRCA2, HER-2, estrogen receptor, progesterone receptor, CA 15-3, CA 27.29, CEA, Ki67, cyclin D1, cyclin E, and ERβ. Exemplary biomarkers for lung cancer include, without limitation, CA 125, CA 15-3, EGF receptor, anaplastic lymphoma kinase gene, MET, ROS-1, and KRAS. Potentially predictive cancer biomarkers include, without limitation, mutations in genes BRCA1 and BRCA2 for breast cancer and/or ovarian cancer, overexpression of CEA, NSE, CYFRA-21-1, CA-125, and CA-199 for lung cancer, overexpression of TYMS, mutations in genes p53 and KRAS for colon cancer.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, the concentration of the biomarker is measured before and after the administration. When the concentration of the biomarker is maintained, the method may further comprise increasing the effective amount of the $PtL_2Cl_2$ by at least 5%, at least 10%, or at least 30%, up to 50%, up to 60%, or up to 80% of an initial effective amount that is in a range of 1-300 mg/kg per body weight of the subject. The increased effective amount may be in a range of 1.05-540 mg/kg, preferably 15-420 mg/kg, more preferably 25-270 mg/kg. The subject may be administered with the increased dosage for a longer period (e.g. 1 week more, 2 weeks more, or 2 months more) than the duration prescribed with the initial effective amount.

In some embodiments, the mutation in the biomarker is detected before administering the composition to identify subjects predisposed to the disease. For example, subjects with a BRCA1 germline mutation are at a higher risk of contracting breast cancer, or ovarian cancer. In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

Having generally described this disclosure, a further understanding can be obtained by reference to certain specific examples which are provided herein for purposes of illustration only and are not intended to be limiting unless otherwise specified.

EXAMPLE 1

Materials and Methods

Chemicals: Potassium tetrachloridoplatinate(II), $K_2PtCl_4$, was obtained from Strem Chemicals, Inc., USA. Deuterated solvents and dimethylsulfoxide (DMSO) were purchased from Sigma Aldrich Chemical Co. The selenone ligands were prepared according to the procedure already described in the literature [Cristiani et al. J. Chem. Soc. Perkin Trans. II, (1977) 324; and Wazeer iet al. Magn. Reson. Chem. 2003, 41, 1026-1029 each incorporated by reference in their entirety].

Cell Cultures: Human Cervical cancer HeLa and Brest cancer cell lines MCF-7 were grown in Dulbecco's modified Eagle's medium (DMEM) supplemented with 10% Fetal Bovine Serum (FBS), and 1% penicillin (10,000 units), streptomycin (10 mg), in 74 cm2 flask and incubated until 80% confluences obtained in humidified environment of, 5% CO2, 95% air, 37° C.

Instrumentation: Elemental analyses of the complexes were carried out on Perkin Elmer 2400 series II CHNS/O Elemental Analyzer. The Infrared spectra of selenone ligands and their platinum(II) complexes were recorded on a Nicolet 6700 FTIR spectrometer using KBr pellets from 4000 to 400 cm$^{-1}$. The $^1H$ (500.01 MHz), $^{13}C$ (125.65 MHz) and $^{77}Se$ (200.0 MHz) NMR spectra were recorded on a LAMBDA 500 MHz NMR spectrometer. The $^1H$ and $^{13}C$ chemical shifts were referenced with respect to tetramethylsilane (TMS), while for $^{77}Se$ NMR, $NaHSeO_3$ (1308 ppm) was used as an external standard.

EXAMPLE 2

Synthesis of the $PtL_2Cl_2$ Complexes

The chemical structure of the selonone ligands used are shown below.

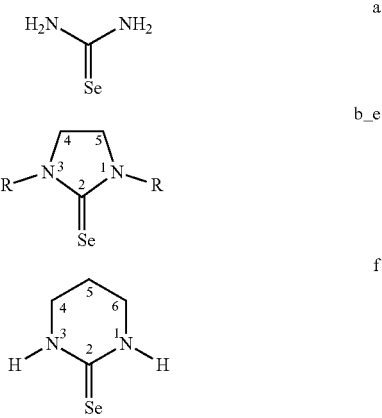

Scheme 1

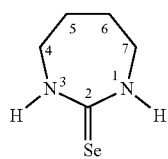

g a) (SeU), Selenourea ($CH_4N_2Se$)
b) (ImSe), [R=R/=H; Imidazolidine-2-selone]
c) (EtImSe), [R=$C_2H_5$, R/=H; N-ethylimidazolidine-2-selone]
d) (PrImSe), [R=$C_3H_7$, R/=H; N-propylimidazolidine-2-selone]
e) (i-PrImSe), [R=i-$C_3H_7$, R/=H; N-(i-propyl)imidazolidine-2-selone]
f) (DiazSe), [1,3-Diazinane-2-selone]
g) (DiapSe), [1,3-Diazipane-2-selone]

The $PtL_2Cl_2$ complexes 1-7, wherein L is having the chemical structure (a)-(g), respectively, were synthesized in the same manner. The free selonone compounds are labile in the presence of oxygen and water. Thus, all solvent used in the synthesis were dried and degassed. In a typical synthesis of the complexes, one mmol of selenone in 25 ml methanol is added to 103.75 mg (0.5 mmol) of potassium tetracholoridoplatinate(II) dissolved in hot acetonitrile under nitrogen and the reaction mixture is stirred for one hour in a dry box. The $PtL_2Cl_2$ complex precipitated and isolated from the reaction mixture by filtration in 60-80% yield. The colored precipitates are sufficiently stable and can be handled in the air. The elemental analyses, melting points, and colors of the complexes are summarized in Table 1.

TABLE 1

Elemental analyses and melting points (° C.) of $PtL_2Cl_2$ complexes.

| Complex | Found (Calcd.) (%) | | | Melting point (° C.) | Color |
| --- | --- | --- | --- | --- | --- |
| | C | H | N | | |
| Pt(SeU)$_2$Cl$_2$ (1) | 4.69 (4.72) | 1.57 (1.39) | 10.94 (10.56) | 191-192 | Black |
| Pt(ImSe)$_2$Cl$_2$ (2) | 12.77 (12.89) | 2.14 (2.27) | 9.93 (10.19) | 226-229 | Yellow |
| Pt(EtImSe)$_2$Cl$_2$ (3) | 19.36 (19.85) | 3.25 (3.38) | 9.03 (9.20) | 195-198 | Yellow |
| Pt(PrImSe)$_2$Cl$_2$ (4) | 22.23 (22.75) | 3.73 (3.87) | 8.64 (8.98) | 161-163 | Brown |
| Pt(i-PrImSe)$_2$Cl$_2$ (5) | 22.23 (19.85) | 3.73 (3.38) | 8.64 (9.20) | 178 (decom) | Brown |
| Pt(DiazSe)$_2$Cl$_2$ (6) | 16.22 (15.96) | 2.72 (2.58) | 9.46 (9.04) | 183-186 | Orange |
| Pt(DiapSe)$_2$Cl$_2$ (7) | 19.36 (20.18) | 3.25 (3.43) | 9.03 (8.78) | 215-218 | Brown |

EXAMPLE 4

Spectroscopic Characterization of the Complexes (a) IR Spectroscopy

Table 2 lists the significant IR bands of free selones and their platinum(II) complexes. The $\nu(C=Se)$ vibration, which occurs around 600 cm$^{-1}$ for free ligands shifted towards the lower frequency region upon complexation as observed for other selenone complexes [Ahmad et al. Polyhedron, 21, 2099-2105 (2002); Ahmad et al. Inorg. Chem. Commun. 5 (2002) 355; Ahmad et al. J. Coord. Chem., 2003, Vol. 56, No. 6, pp. 539-544; Isab et al. Polyhedron, 25, 2629-2636 (2006)]. The $\nu(N-H)$ and $\nu(C-N)$ bands around 3200 cm$^{-1}$ and 1500 cm$^{-1}$ respectively, shifted to higher wave numbers upon coordination. The appearance of these bands indicates the complexation of selones to platinum(II).

TABLE 2

Selected IR absorptions (cm$^{-1}$) of selones and their complexes.

| Species | IR frequencies (cm$^{-1}$) | | |
| --- | --- | --- | --- |
| | $\nu(C=Se)$ | $\nu(C-N)$ | $\nu(N-H)$ |
| SeU | 736 | 1520 | 3265 |
| (1) | 560 | 1565 | 3267 |
| ImSe | 561 | 1463 | 3250 |
| (2) | 513 | 1499 | 3325 |
| EtImSe | 514 | 1465 | 3198 |
| (3) | 479 | 1479 | 3265 |
| PrImSe | 513 | 1460 | 3210 |
| (4) | 492 | 1497 | 3343 |
| i-PrImSe | 601 | 1453 | 3210 |
| (5) | 556 | 1486 | 3267 |
| DiazSe | 601 | 1430 | 3200 |
| (6) | 561 | 1469 | 3267 |
| DiapSe | 615 | 1453 | 3224 |
| (7) | 510 | 1459 | 3350 |

(b) NMR Spectroscopy

The $^1H$ NMR chemical shifts of platinum(II) complexes in DMSO-$d_6$ are given in the Table 3. In proton NMR, the N—H signal became less intense and shifted slightly downfield by 0.8 to 1.2 ppm upon coordination to platinum. These shifts were attributed to the shift of the electron density from nitrogen to carbon producing a partial double bond character in the C—N single bond. This downfield shift is characteristic of the selones ligated to Pt(II) ion through the selenium atoms and not via nitrogen atoms [Ahmad et al. Polyhedron, 21, 2099-2105 (2002); Ahmad et al. Inorg. Chem. Commun. 5 (2002) 355; Ahmad et al. J. Coord. Chem., 2003, Vol. 56, No. 6, pp. 539-544; Isab et al. Polyhedron, 25, 2629-2636 (2006)].

The $^{13}C\{^1H\}$ NMR chemical shifts for free selones and their corresponding platinum complexes are summarized in Table 3. For all compounds, the selenocarbonyl (C=Se) resonance of selones shifted upfield by 2.7 to 14 ppm relative to their positions in uncoordinated ligands. This shows a good consistency with the reported literature [Ahmad et al. Polyhedron, 21, 2099-2105 (2002); Ahmad et al. Inorg. Chem. Commun. 5 (2002) 355; Ahmad et al. J. Coord. Chem., 2003, Vol. 56, No. 6, pp. 539-544; Isab et al. Polyhedron, 25, 2629-2636 (2006)]. The upfield shift assigned for the C-2 resonance is due to the lowering of C=Se bond order upon coordination and a shift of N→C electron density producing a partial double bond character in the C—N bond. The upfield shifts imply that the coordination of selones to Pt(II) ion occurs via selenium atom [Sadaf et al. Mol. Struc. 1085 (2015) 155-161; Ahmad et al. Polyhedron, 21, 2099-2105 (2002); Ahmad et al. Inorg. Chem. Commun. 5 (2002) 355; Ahmad et al. J. Coord. Chem., 2003, Vol. 56, No. 6, pp. 539-54)]. The increased electron density of the C—N bond upon coordination to platinum results in minor increases in deshielding effects on C-4 and C-5, as observed by downfield shifts in these resonances.

TABLE 3

$^1$H and $^{13}$C{$^1$H} chemical shifts of Pt(II) complexes with selones in DMSO-d$_6$.

| Species | N—H | C-2 | C-4 | C-5 | C-6 | C-7 | N—C1 | N—C2 | CH3 |
|---|---|---|---|---|---|---|---|---|---|
| SeU | 7.59 | 178.83 | — | — | — | — | — | — | — |
| (1) | 8.59 | 168.02 | — | — | — | — | — | — | — |
| Δ | 1.00 | −10.83 | — | — | — | — | — | — | — |
| ImSe | 8.32 | 177.05 | 45.26 | 45.26 | — | — | — | — | — |
| (2) | 9.47 | 163.08 | 45.64 | 45.64 | — | — | — | — | — |
| Δ | 1.15 | −13.97 | 0.38 | 0.38 | — | — | — | — | — |
| Et-ImSe | 8.32 | 178.66 | 43.33 | 47.91 | — | — | 42.51 | — | 12.09 |
| (3) | 9.15 | 174.59 | 43 | 48.38 | — | — | 42.9 | — | 12.19 |
| Δ | 0.83 | −4.07 | −0.33 | 0.47 | — | — | 0.39 | — | 0.10 |
| PrImSe | 8.81[b] | 179.55[c] | 50.19 | 48.62 | — | — | 42.60 | 10.99 | 10.99 |
| (4) | 9.85 | 176.65 | 52.21 | 49.85 | — | — | 43.27 | 21.32 | 11.21 |
| Δ | 1.04 | −2.90 | 2.02 | 1.23 | — | — | 0.67 | 0.95 | 0.22 |
| i-PrImSe | 8.26 | 177.71 | 42.65 | 42.69 | — | — | 48.21 | — | 19.45 |
| (5) | 9.44 | 167.47 | 44.00 | 43.58 | — | — | 48.35 | — | 19.65 |
| Δ | 1.18 | −10.24 | 1.35 | 0.89 | — | — | 0.14 | — | 0.20 |
| DiazSe | 8.07 | 169.07[a] | 40.36 | 18.88 | 40.36 | — | — | — | — |
| (6) | 9.30 | 160.48 | 40.26 | 18.46 | 40.26 | — | — | — | — |
| Δ | 1.23 | −8.59 | −0.10 | −0.42 | −0.10 | — | — | — | — |
| DiapSe | 8.07 | 180.83 | 45.5 | 26.86 | 26.86 | 45.5 | — | — | — |
| (7) | 9.16 | 171.71 | 46.78 | 26.4 | 26.4 | 46.78 | — | — | — |
| Δ | 1.09 | −9.12 | 1.28 | −0.46 | −0.46 | 1.28 | — | — | — |

[a]Dissolved in D$_2$O,
[b]From the literature and
[c]Dissolved in CDCl$_3$

The $^{77}$Se NMR chemical shifts are presented in Table 4. In $^{77}$Se NMR significantly large upfield shifts (17.5 to 76.2 ppm) were observed for the selones upon complexation [Ahmad et al. Polyhedron, 21, 2099-2105 (2002); Ahmad et al. Inorg. Chem. Commun. 5 (2002) 355]. This very large shielding provides a clear evidence for selenium binding to the metal center. The DiapSe complex shows the highest shift difference of 76 ppm suggesting that this would be the most stable among the prepared complexes. This trend is not consistent with the $^{13}$C NMR data, where the ImSe shows the greatest difference.

TABLE 4

$^{77}$Se{$^1$H} chemical shifts (δ) of Pt(II) complexes with selones in DMSO-d$_6$.

| Species | Chemical shifts |
|---|---|
| (SeU) | 200.70 |
| (1) | 149.60 |
| Δ | −51.12 |
| ImSe | 73.53 |
| (2) | 48.52 |
| Δ | −25.01 |
| EtImse | 64.85 |
| (3) | 47.35 |
| Δ | −17.5 |
| N-PrImSe | 57.93 |
| (4) | 26.91 |
| Δ | −31.02 |
| i-PrImSe | 69.29 |
| (5) | 29.5 |
| Δ | −39.79 |
| DiazSe | 199.93 |
| (6) | 126.35 |
| Δ | −73.58 |
| DiapSe | 292 |
| (7) | 215.75 |
| Δ | −76.25 |

The proposed structure for the platinum (II) selone complex of compound 2 is:

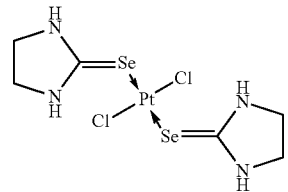

EXAMPLE 5

Measurement of Anticancer Activity of Compound 1-7
MTT Assays for Anticancer Activity of Platinum Complexes 1-7

Complexes 1-7 and cisplatin (positive control) at 0.195 μM, 0.39 μM, 0.781 μM, 1.56 μM, 3.125 μM, 6.25 μM, 12.5 μM, 25 μM, and 50 μM concentrations were prepared in DMEM. Cancer cells were seeded and maintained in quadruplicate in a 96-well tissue culture plate at 5×10$^4$ cells per well in 200 μl of same medium. The cancer cells were incubated 24 hours before the treatment. All compounds were dissolved in 50% DMSO. Therefore, DMSO was used as a negative control. The final DMSO concentration, in each well, was less than 0.1%. The cancer cells were treated with the synthesized compounds 1-8 along with the cisplatin and the resultant cultures were incubated for 24 h. The medium of wells was discarded and 100 μL DMEM containing MTT (3-(4,5-dimethylthiazol-2-yl)-2,5-diphenyltetrazolium bromide) (5 mg/mL) was added to the wells and incubated in a CO$_2$ incubator at 37° C. in the dark for 4 hrs. After incubation, a purple colored formazan (artificial chromogenic dye, a product of the reduction of water insoluble tetrazolium salts e.g., MTT by dehydrogenases and reductases) in the cells is produced and appeared as dark crystals in the bottom of the wells. The medium of culture was discarded from each well carefully to avoid disruption of the monolayer. 100 μL of isopropanol was added in each well. The solution was thoroughly mixed in the wells to dissolve the formazan crystals which ultimately results into a purple solution. The absorbance of the 96-well plate was measured at 570 nm with Mithras2LB943 against reagent blank. All data presented are mean±standard deviation.

In Vitro Cytotoxicity

To examine the possible anticancer effect of cisplatin and the prepared complexes, two human tumor cell lines, HeLa (cervical cancer cells) and MCF7 (breast cancer cells) were used. The results of in vitro cytotoxic activity are expressed as $IC_{50}$ (concentration causing 50% reduction in cell viability) and are presented in Table 5. It can be seen that the $IC_{50}$ values of the investigated complexes are better than or comparable to that of cisplatin. Except ImSe complex, all complexes showed anticancer effect against HeLa cells better than cisplatin, while three out of seven complexes are more effective against MCF7 cells. Among the complexes, the DiazSe complex (6) exhibited the strongest antiproliferative potency in HeLa cells, while ImSe compound (2) was the most active for MCF7 cells (Table 5).

Figure 2:
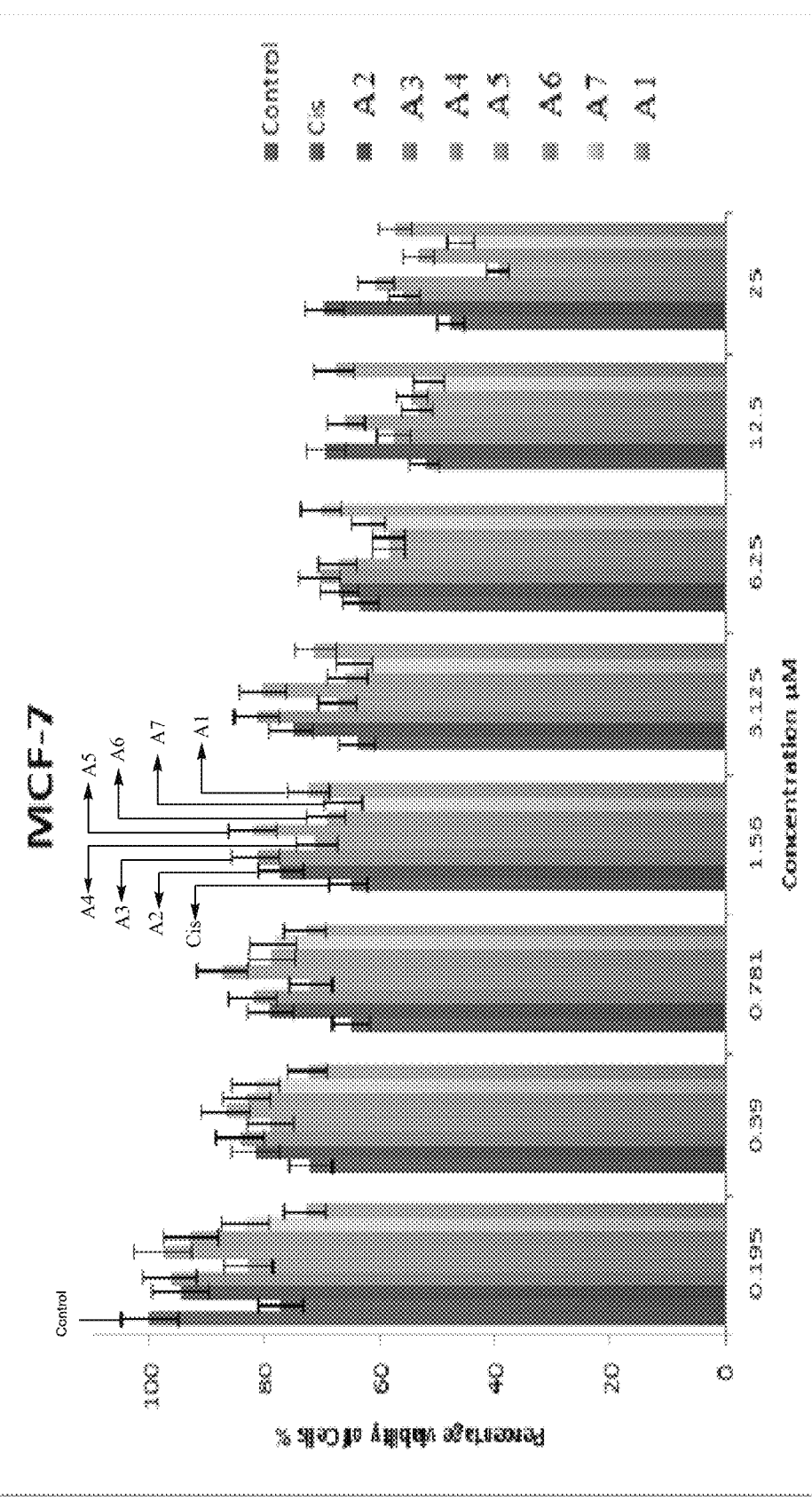
FIG. 2: Effect of concentration of PtL$_2$Cl$_2$ complexes, wherein L is selected from compounds 1-7, and cisplatin (Cis) in μM on the percentage viability of MCF7. The complexes are designated A1-A7 in the Figure.

The survival of the cells (HeLa and MCF7) was studied by varying the concentration of compounds. The percentage of cell viability at various concentrations of platinum(II) compounds is shown in FIGS. 1 and 2. The data obtained represents the concentration dependent cytotoxic effect against the human cancer cells. As the concentration decreases the cell viability increases.

TABLE 5

In vitro cytotoxicity of the complexes and cisplatin given as $IC_{50}$ ± S.D. in µM.

| Compound | $IC_{50}$ ± SEM[a] | |
|---|---|---|
| | HeLa | MCF7 |
| Cisplatin | 21.40 ± 0.73 | 8.98 ± 0.07 |
| (1) | 19.78 ± 0.13 | 11.11 ± 0.05 |
| (2) | 25.74 ± 0.19 | 8.11 ± 0.06 |
| (3) | 17.73 ± 0.14 | 8.59 ± 0.07 |
| (4) | 12.89 ± 0.16 | 18.64 ± 0.03 |
| (5) | 14.03 ± 0.16 | 8.30 ± 0.06 |
| (6) | 11.33 ± 0.20 | 12.27 ± 0.01 |
| (7) | 11.50 ± 0.22 | 16.68 ± 0.02 |

[a]Limit of errors is given in SEM as standard deviations determined from at least three independent experiments.

The invention claimed is:

1. A platinum (II) complex of formula $PtL_2Cl_2$, wherein L is of formula Ia, Ib, Ic, or Id:

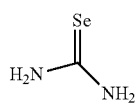

Ia

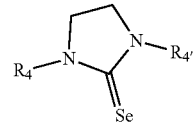

Ib

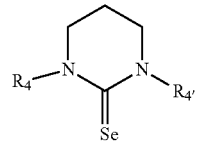

Ic

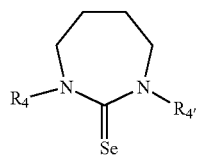

Id wherein $R_4$ and $R_{4'}$ are independently hydrogen, methyl, ethyl, propyl, isopropyl, butyl, isobutyl, t-butyl, pentyl, isopentyl, phenyl, or benzyl.

2. A method of making the platinum (II) complex of claim 1, said method comprising:
   (a) adding a solution of tetrahaloplatinate (II) in a polar aprotic solvent to a solution of a compound of formula Ia, Ib, Ic, or Id in a solvent under inert gas to form a reaction mixture, and
   (b) stirring the reaction mixture to form the platinum (II) complex as a precipitate.

3. The method of claim 2, further comprising filtering the platinum (II) complex.

4. A pharmaceutical composition comprising the platinum (II) complex of claim 1; and a pharmaceutically acceptable carrier and/or excipient.

5. The pharmaceutical composition of claim 4, which comprises 0.1-400 µM of the platinum (II) complex relative to the total volume of the composition.

6. The pharmaceutical composition of claim 5, wherein the pharmaceutically acceptable carrier and/or excipient is at least one selected from the group consisting of a buffer, an inorganic salt, a fatty acid, a vegetable oil, a synthetic fatty ester, a surfactant, and a polymer.

7. The pharmaceutical composition of claim 5, further comprising a chemotherapeutic agent.

8. A method for treating cervical cancer, breast cancer, or both in a subject in need of therapy, the method comprising administering to the subject a sufficient amount of the pharmaceutical composition of claim 4.

9. The method of claim 8, wherein 1-300 mg/kg of the platinum (II) complex is administered per body weight of the subject.

10. The method of claim 8, wherein the subject is a mammal.

* * * * *